US011998368B2

United States Patent
Irish et al.

(10) Patent No.: US 11,998,368 B2
(45) Date of Patent: Jun. 4, 2024

(54) IMAGE CAPTURE SYSTEM USING AN IMAGER CODE SCANNER AND INFORMATION MANAGEMENT SYSTEM

(71) Applicant: Draeger Medical Systems, Inc., Andover, MA (US)

(72) Inventors: Mark Irish, Moorestown, NJ (US); Carl Sisco, Milan, TN (US); Jody Bardman, Green Lane, PA (US)

(73) Assignee: Draeger Medical Systems, Inc., Andover, MA (US)

( * ) Notice: Subject to any disclaimer, the term of this patent is extended or adjusted under 35 U.S.C. 154(b) by 340 days.

(21) Appl. No.: 16/812,918

(22) Filed: Mar. 9, 2020

(65) Prior Publication Data
US 2020/0281542 A1    Sep. 10, 2020

Related U.S. Application Data

(60) Provisional application No. 62/815,646, filed on Mar. 8, 2019.

(51) Int. Cl.
*A61B 5/00* (2006.01)
*A61B 5/318* (2021.01)
(Continued)

(52) U.S. Cl.
CPC ............ *A61B 5/7495* (2013.01); *A61B 5/318* (2021.01); *G16H 10/60* (2018.01); *G16H 30/40* (2018.01)

(58) Field of Classification Search
None
See application file for complete search history.

(56) References Cited

U.S. PATENT DOCUMENTS

2011/0237940 A1*  9/2011  Raleigh .............. A61B 1/00177
                                          600/425
2011/0316704 A1* 12/2011  Nielsen ................ A61B 5/0002
                                          702/187
(Continued)

FOREIGN PATENT DOCUMENTS

GB           2420893 A  *  6/2006  ............. A61B 5/117

OTHER PUBLICATIONS

Abedtash, Hamed. "An Interoperable Electronic Medical Record-Based Platform for Personalized Predictive Analytics." Order No. 10602258 Indiana University—Purdue University Indianapolis, 2017. Ann Arbor: ProQuest. Web. Jan. 18, 2024. (Year: 2017).*

*Primary Examiner* — Lena Najarian
(74) *Attorney, Agent, or Firm* — Design IP

(57) ABSTRACT

An electronic medical record (EMR) management system includes an imager code scanner having a user input mechanism and is configurable in a plurality of operation modes, including a code scanning mode and an image capture mode. In the code scanning mode, the imager code scanner is configured to detect a two-dimensional code and output symbology code information representative of the detected two-dimensional code in response to a user input mechanism being engaged. In the image capture mode, the imager code scanner is configured to output a captured image in response to the user input mechanism being engaged. The EMR management system further includes an information management system communicatively coupled to the imager code scanner. The information management system is configured to receive the captured image output from the imager code scanner and incorporate the captured image into an EMR corresponding to a patient.

18 Claims, 5 Drawing Sheets

(51) Int. Cl.
*G16H 10/60* (2018.01)
*G16H 30/40* (2018.01)

(56) References Cited

U.S. PATENT DOCUMENTS

| | | | | |
|---|---|---|---|---|
| 2012/0242501 | A1* | 9/2012 | Tran | A61B 5/4875 340/870.02 |
| 2012/0290957 | A1* | 11/2012 | Chernilo | G16H 40/63 715/764 |
| 2013/0092727 | A1* | 4/2013 | Edwards | G06K 15/024 235/375 |
| 2015/0193579 | A1* | 7/2015 | Bruce | H04L 67/14 705/2 |
| 2020/0175236 | A1* | 6/2020 | Barkan | G06K 7/1408 |

* cited by examiner

FIG. 2

IMAGE CAPTURE SYSTEM USING AN IMAGER CODE SCANNER AND INFORMATION MANAGEMENT SYSTEM

CROSS-REFERENCE TO RELATED APPLICATIONS

This application claims the benefit of U.S. Provisional Application Ser. No. 62/815,646 filed on Mar. 8, 2019, which is incorporated by reference as if fully set forth.

BACKGROUND

Electronically capturing images during medical examinations, medical procedures, such as surgeries, patient treatment, and patient monitoring for input into a patient's electronic medical record is a challenge for any medical documentation application. Currently, health care providers may use manual methods such as physically printing out a medical measurement reading, taping the printout to a paper record, and scanning the taped document to create an electronic document that can be input and stored into an Electronic Medical Record (EMR). This process is cumbersome, time-consuming, and susceptible to errors and omissions. Furthermore, this process may not be feasible or may be prohibited in certain environments, such as an operating room (OR).

For example, electrocardiogram (ECG) machines record the electrical signals of a heart. Many ECG machines are capable of displaying the electrical reading in real-time on a display and printing the electrical reading on a tracing strip that includes 10 to 12 heartbeats. Health care providers would like to capture and document ECG tracing strips or other images in a patient's EMR such as, but not limited to, anesthesia software, immediately prior to the start of surgery or any other time during patient care. The requirement to capture this data in the EMR is becoming increasingly important for medical and legal reasons as well as for reporting purposes, rather than primarily for diagnostic or therapeutic purposes. For example, with regard to capturing the ECG strip, the intent is to illustrate the general heart rhythm condition of the patient prior to surgery.

Additionally, there may be a desire to facilitate the integration of other types of images into a patient's EMR.

SUMMARY

One or more embodiments provide an electronic medical record (EMR) management system, including: a data server configured to store an EMR of a patient; an imaging device configured to capture an image medically related to the patient and transmit the captured image; and an information management system communicatively coupled to the imaging device and to the data server. The information management system is configured to receive the captured image from the imaging device, automatically associate the captured image to the patient, and store the captured image in the EMR of the patient in the data server.

One or more embodiments provide a method of recording medical image data using an imaging device being configured to capture and output images. The method includes initializing, by a user interface system, an image capture session in response to a first user input; generating, by the imaging device, a captured image in response to a second user input; automatically transmitting, by the imaging device, the captured image to the user interface system in response to generating the captured image, wherein the captured image is medically related to a patient; automatically associating, by the user interface system, the captured image to the patient upon receipt; and storing, by the user interface system, the received captured image in an electronic medical record (EMR) of the patient associated with the captured image.

One or more embodiments provide a method of recording medical image data in an electronic medical record (EMR) associated with a patient using an imaging device being configurable in a plurality of operation modes, including a code scanning mode and an image capture mode, wherein, in the code scanning mode, the imaging device is configured to detect a machine-readable code and output code information representative of the detected machine-readable code, and wherein, in the image capture mode, the imaging device is configured to output a captured image. The method includes initializing, by a user interface system, an image capture session in response to a first user input applied at the user interface system; determining, by the user interface system, a first operation mode of the imaging device, the first operation mode being an active one of the plurality of operation modes at a time the image capture session is initialized; storing, by the user interface system, the first operation mode in a memory device; determining, by the user interface system, whether the first operation mode is an image capture mode; on a first condition that the first operation mode is not the image capture mode, configuring, by the user interface system, the imaging device into the image capture mode; on a second condition that the first operation mode is the image capture mode, maintaining, by the user interface system, the imaging device in the image capture mode; generating, by the imaging device, the captured image in response to a first user input applied at the imaging device; automatically transmitting, by the imaging device, the captured image to the user interface system in response to generating the captured image, wherein the captured image is medically related to the patient; automatically associating, by the the user interface system, the captured image to the patient upon receipt; and storing, by the user interface system, the received captured image in the EMR associated with the patient.

One or more embodiments provide a non-transitory computer-readable medium having computer-readable instructions stored thereon which when executed by a computer system cause the computer system to perform a method of recording medical image data in an electronic medical record (EMR) associated with a patient using an imaging device being configurable in a plurality of operation modes, including a code scanning mode and an image capture mode, wherein, in the code scanning mode, the imaging device is configured to detect a machine-readable code and output code information representative of the detected machine-readable code, and wherein, in the image capture mode, the imaging device is configured to output a captured image. The method includes initializing, by a user interface system, an image capture session in response to a first user input applied at the user interface system; determining, by the user interface system, a first operation mode of the imaging device, the first operation mode being an active one of the plurality of operation modes at a time the image capture session is initialized; storing, by the user interface system, the first operation mode in a memory device; determining, by the user interface system, whether the first operation mode is an image capture mode; on a first condition that the first operation mode is not the image capture mode, configuring, by the user interface system, the imaging device into the image capture mode; on a second condition that the first operation mode is the image capture mode, maintaining, by the user interface system, the imaging device in the image capture mode; generating, by the imaging device, the captured image in response to a first user input applied at the imaging device; automatically transmitting, by the imaging device, the captured image to the user interface system in response to generating the captured image, wherein the captured image is medically related to the patient; automatically associating, by the the user interface system, the captured image to the patient upon receipt; and storing, by the user interface system, the received captured image in the EMR associated with the patient.

BRIEF DESCRIPTION OF THE DRAWINGS

Embodiments are described herein making reference to the appended drawings.

FIG. 2 illustrates a first graphical user interface (GUI) according to one or more embodiments;

DETAILED DESCRIPTION

Figure 1:
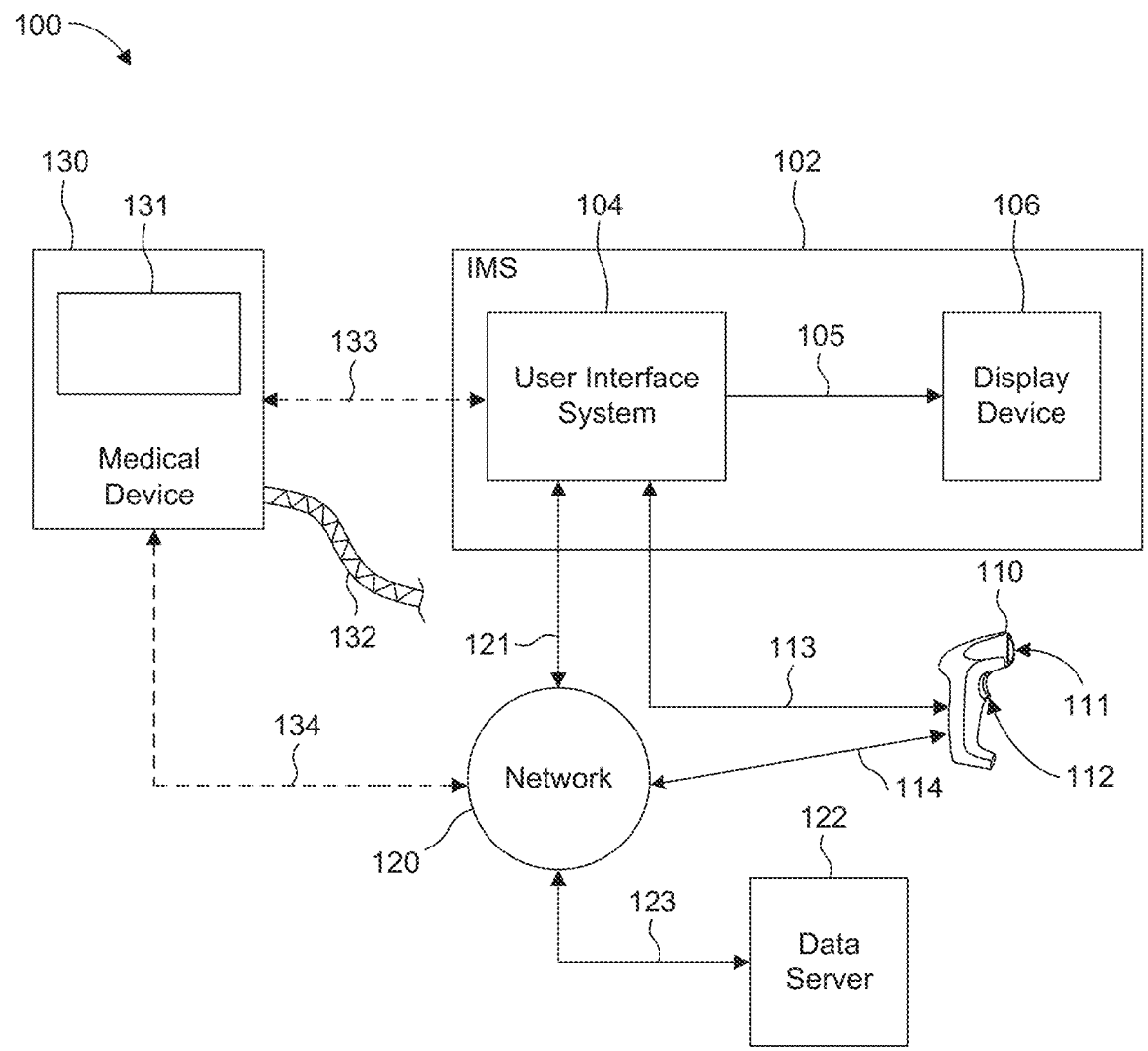
FIG. 1 illustrates a medical system for medical information acquisition and management in accordance with one or more embodiments.

In the following, details are set forth to provide a more thorough explanation of the exemplary embodiments. However, it will be apparent to those skilled in the art that embodiments may be practiced without these specific details. In other instances, well-known structures and devices are shown in block diagram form or in a schematic view rather than in detail in order to avoid obscuring the embodiments. In addition, features of the different embodiments described hereinafter may be combined with each other, unless specifically noted otherwise.

Further, equivalent or like elements or elements with equivalent or like functionality are denoted in the following description with equivalent or like reference numerals. As the same or functionally equivalent elements are given the same reference numbers in the figures, a repeated description for elements provided with the same reference numbers may be omitted. Hence, descriptions provided for elements having the same or like reference numbers are mutually exchangeable.

In this regard, directional terminology, such as "top", "bottom", "below", "above", "front", "behind", "back", "leading", "trailing", etc., may be used with reference to the orientation of the figures being described. Because parts of embodiments can be positioned in a number of different orientations, the directional terminology is used for purposes of illustration. It is to be understood that other embodiments may be utilized and structural or logical changes may be made without departing from the scope defined by the claims. The following detailed description, therefore, is not to be taken in a limiting sense. Directional terminology used in the claims may aid in defining one element's spatial or positional relation to another element or feature, without being limited to a specific orientation.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

In embodiments described herein or shown in the drawings, any direct electrical connection or coupling, i.e., any connection or coupling without additional intervening elements, may also be implemented by an indirect connection or coupling, i.e., a connection or coupling with one or more additional intervening elements, or vice versa, as long as the general purpose of the connection or coupling, for example, to transmit a certain kind of signal or to transmit a certain kind of information, is essentially maintained. Features from different embodiments may be combined to form further embodiments. For example, variations or modifications described with respect to one of the embodiments may also be applicable to other embodiments unless noted to the contrary.

In the present disclosure, expressions including ordinal numbers, such as "first", "second", and/or the like, may modify various elements. However, such elements are not limited by the above expressions. For example, the above expressions do not limit the sequence and/or importance of the elements. The above expressions are used merely for the purpose of distinguishing an element from the other elements. For example, a first box and a second box indicate different boxes, although both are boxes. For further example, a first element could be termed a second element, and similarly, a second element could also be termed a first element without departing from the scope of the present disclosure.

One or more aspects of the present disclosure may be implemented as a non-transitory computer-readable recording medium having recorded thereon a program embodying methods/algorithms for instructing the processor to perform the methods/algorithms. Thus, a non-transitory computer-readable recording medium may have electronically readable control signals stored thereon, which cooperate (or are capable of cooperating) with a programmable computer system such that the respective methods/algorithms are performed. The non-transitory computer-readable recording medium can be, for example, a CD-ROM, DVD, Blu-ray disc, a RAM, a ROM, a PROM, an EPROM, an EEPROM, a FLASH memory, or an electronic memory device.

Each of the elements of the present disclosure may be configured by implementing dedicated hardware or a software program on a memory controlling a processor to perform the functions of any of the components or combinations thereof. Any of the components may be implemented as a central processing unit (CPU) or other processor reading and executing a software program from a recording medium such as a hard disk or a semiconductor memory device. For example, instructions may be executed by one or more processors, such as one or more CPUs, digital signal processors (DSPs), general-purpose microprocessors, application-specific integrated circuits (ASICs), field programmable logic arrays (FPGAs), programmable logic controller (PLC), or other equivalent integrated or discrete logic circuitry. Accordingly, the term "processor," as used herein refers to any of the foregoing structures or any other structure suitable for implementation of the techniques described herein. A controller including hardware may also perform one or more of the techniques of this disclosure. A controller, including one or more processors, may use electrical signals and digital algorithms to perform its receptive, analytic, and control functions, which may further include corrective functions. Such hardware, software, and firmware may be implemented within the same device or within separate devices to support the various techniques described in this disclosure.

It will be appreciated that electrical connections described herein may be a wireless connection, a wired connection, or a combination thereof, and may be further referred to as a communication channel. A communication channel may be any known type of communication channel, non-limiting examples of which include wired communication such as coaxial cable and fiber-optic link to allow communication via Ethernet, and the like, wireless communication such as wireless network (IEEE 802.XX), cellular data service (3G/4G/5G), short-range communication technologies (e.g., Bluetooth, RFID, NFC, Zigbee), and the like and combinations thereof of wired communication and wireless communication, which enable transfer of information between connected devices. However, one of ordinary skill in the art would understand that the communication channels are not limited to these examples, and the communication channels could be implemented by other means within the capabilities of one of ordinary skill in the art.

As stated above, electronically capturing an ECG tracing or other images such as pictures or ultrasound snapshots for input into any electronic record is a challenge. For example, there currently is no single standard for capturing ECG tracings and each brand of patient monitors uses their own proprietary protocols and practices. Moreover, a typical surgical suite has a plurality of different manufactured devices that capture output which needs to be implemented into the EMR system.

In addition, it may be desirable to acquire images of a patient to document a patient's current condition and store the images in the EMR. The images may be used to document a region of interest, for example, a dental condition prior to intubation or a surgical site prior to and/or subsequent to performing a medical procedure in order to establish a patient record of the procedure. However, a process for creating this electronic record is lacking. Furthermore, current information management systems do not enable easy and rapid retrieval of this information.

In addition, the ability to scan codes located on patient wristbands, medical equipment, medication, and medical fluid bags, such as intravenous (IV) fluid bags, blood bags, and other types of medicine bags or drip bags may be desirable. Such scanning may be useful for at least one of the following identification (ID): patient ID, equipment ID, medication ID, medical device ID (e.g., settings, implants, readouts, or the like), and medical fluid bag ID and entering such ID information into the patient's EMR.

Therefore, an image capturing system configured to capture both images and ID information for generating medical data, associating the generated medical data to a patient, and storing the medical data into the associated patient's EMR may be desirable. An information management system that can be used to manage this medical data may also be desirable.

One or more embodiments are directed to the capture of electronic images and/or videos using an imager to generate medical data that is associated with and ultimately stored in a patient's Electronic Medical Record (EMR) and accessed and managed therefrom. An imager may be any imaging device capable of capturing an image, a video or audio, and includes by is not limited to a scanner, a camera, a phone, a tablet, a wearable device, a medical diagnostic device, a medical monitoring device, a medical therapeutic device, and the like. In one example, an imager may be a code scanner or code reader that is configured to scan or read machine-readable codes, such as one-dimensionally symbologies (e.g., barcodes), two-dimensional symbologies (e.g., Quick Response (QR) codes), radio-frequency identification (RFID) tags, or the like, as well as capture images. In another example, an imager may be a medical device the includes a display (e.g., a medical diagnostic device, a medical monitoring device, a medical therapeutic device) that is capable of capturing screen images from the display (e.g., screenshots). In another example, an imager may be a medical device that is capable of outputting an image of medical data regardless of whether the medical device includes a display or not.

In the case that the imager is a code scanner, the code scanner includes a digital camera configured to obtain a digital image in response to user input, such as a user interacting with, manipulating, or otherwise engaging a button or a trigger mechanism.

The code scanner is selectively configurable in a code scanning mode and an image capture mode. During the code scanning mode, the code scanner is configured to analyze a machine-readable code and output code information. In the image capture mode, the code scanner is configured to capture an image and output the image, for example, without image processing and/or analysis. The code scanner may be communicatively coupled by an electrical connection to an information management system and may transmit data, including code information or a captured image, to the information management system. The information management system may be a computing system or other processing system that acquires code information and captured images and automatically associates at least the captured images to a patient and provides further options to store the captured images in the patient's EMR. The information management system may also automatically associate code information to a patient and provides further options to store the code information in the patient's EMR. The information management system may also be configured to automatically store the captured image in the patient's EMR in response to the information management system associating the captured image with the patient.

According to one example of code scanning mode, the code scanner is configured to acquire a digital image and analyze the digital image to detect the machine-readable code. In particular, the code scanner may be configured to read and identify machine-readable codes in the digital image, and generate code information representative of the scanned machine-readable code. The code information may be a unique sequence of numbers, characters, and/or bits. Thus, the code information is data representative of the unique machine-readable code. The code information may then be output from the code scanner to the information management system and/or to a database (e.g., a record system). The information management system or the database may then store the code information and/or convert the code information into identification (ID) information corresponding to a patient ID, equipment ID, medication ID, medical fluid bag ID, and the like, by cross-referencing the code information with ID information stored in the database. In particular, ID information stored in the database may be linked to a unique code, and the information management system may search the database for corresponding ID information based on the code information received from the code scanner.

The code scanner may be used to scan a code and characters corresponding thereto may be automatically inserted into a text field in a GUI.

For patient identification, a code may include a prefix or suffix that indicates that the code corresponds to patient identification. The information management system receives the code information from the code scanner and determines whether the code information includes the pre-assigned prefix or suffix that indicates that the code corresponds to a patient ID. If the prefix or suffix is present, the information management system identifies the patient according to the patient ID extracted from the code information. If the prefix or suffix is not present, the information management system determines that the code is not related to a patient ID, but instead related to another information type, for example, to a different ID type or to information to be inserted into a text field.

In image capture mode, the code scanner is configured to acquire a digital image and output the digital image into the information management system and/or the database. In this mode, the digital image is acquired and output without performing code recognition and analysis.

In one example, the code scanner may be used to capture electronic ECG tracings directly printed ECG tracings or from capturing an image of the ECG monitor. Given that health care providers may use a variety of—manufacturer-branded ECG monitors, the code scanner provides a viable solution for capturing of ECG tracings regardless of the manufacturer and for inputting the electronic ECG tracing into the patient record.

As a result, the code scanner may be incorporated into an image capturing system configured to capture both medical images and medical ID information for generating medical data, associating the medical data with a patient, and storing the medical data into the patient's EMR. Further embodiments also provide an information management system that can be used to access and manage these medical data. Medical images may include images generated by medical imaging devices related, but not limited to, magnetic resonance imaging (MM), X-ray, positron emission tomography (PET) scan, computerized tomography (CT), ultrasound, dye imaging, and Electrical Impedance Tomography (EIT) imaging. In addition, medical images may include images of medical data in printable forms, such as printed ECG waveforms, and images associated with a patient (dental, body surface, implanted device, etc.).

FIG. 1 illustrates a medical system 100 for medical information acquisition and management in accordance with one or more embodiments. The medical system 100 includes an information management system (IMS) 102 comprising a user interface system 104 and a display device 106. The user interface system 104 may be a computer having one or more processors and tangible computer-readable media for carrying or having computer-executable instructions or data structures stored thereon. For example, user interface system 104 may store or have access to EMR software used for acquiring, accessing, and managing medical data pertaining to one or more patients.

The user interface system 104 may also include one or more input devices, such as a keyboard, mouse, or a touchscreen, configured to be manipulated by a user for receiving user input.

The user interface system 104 may also include a controller configured to control one or more aspects of the user interface system 104 and/or an imager. For example, the controller may be integrated with a means for receiving user input and control one or more graphical user interfaces (GUIs) based on user input. Additionally, or alternatively, the controller may control one or more functions of an imager communicatively coupled to the user interface system 104 based on user input.

The user interface system 104 is operable to acquire and store patient data and other medical data, as well as to retrieve patient data and other patient data, and may further provide user interface instructions to one or more system components. The user interface system 104 is operable to receive captured images and automatically associate the captured images to a patient and provides further options to store the captured images in the patient's EMR. The user interface system 104 may be configured to transmit the captured images to a database or a data server 122 to be stored in the patient's EMR in response to a user input that follows the user interface system 104 associating the captured images to a patient. Alternatively, the user interface system 104 may be configured to automatically transmit the captured images to a database or a data server 122 to be stored in the patient's EMR in response to the user interface system 104 associating the captured image with the patient. The user interface system 104 may also be operable to receive code information, automatically associate the code information to a patient, and provide further options to store the code information in the patient's EMR.

The user interface system 104 is further operable to generate display data, such as one or more GUIs to be displayed on the display device 106. A GUI may be used for the entering, storing, and retrieval of patient data and other medical data.

The display device 106 is any type of display or screen operable to display image data, including GUIs, captured images, and other data. The display device 106 is coupled to the user interface system 104 via connection 105 and is configured to display image data received from the user interface system 104. For example, the display device 106 may be configured to display image data corresponding to the EMR software, including, but not limited to, GUIs, menu windows, application windows, dialog boxes, patient records and data, medical images, and the like.

The medical system 100 may include a code scanner 110 that is configurable in at least a code scanning mode and an image capture mode, as described above. While some embodiments may be described in the context of a code scanner 110, it will be appreciated that other types of imagers capable of capturing images may be used. It will also be appreciated that while some types of imagers are capable of reading machine-readable codes, other types of images may not be configured with such functionality. Thus, the code scanner 110 is merely representative of one type of portable image capture device and other portable image capture devices may be used in the alternative to or in addition to the code scanner.

With respect to the code scanner 110, the code scanner may be any type of imager that uses a camera to capture a digital image, detect a machine-readable code in the digital image, generate code information therefrom, and transmit the code information. The code scanner 110 includes a digital camera 111 and a user input element 112 (e.g., a button or trigger mechanism) configured to trigger an image acquisition of the digital camera 111 in response to user input.

The code scanner 110 may be coupled to the user interface system 104 via connection 113, which may be a wired communication channel or a wireless communication channel. In particular, the code scanner 110 may receive control signals from the user interface system 104 to control and/or switch its operating mode. Thus, control signals may be received that configures the code scanner 110 into either the code scanning mode or the image capture mode.

Additional mechanisms for changing the operation mode of the code scanner 110 may also be provided. For example, machine-readable configuration codes may be used to trigger an operation mode reconfiguration of the code scanner 110. For example, a machine-readable configuration code may be provided for each operation mode of the code scanner. When a machine-readable configuration code is read by the code scanner 110, the read machine-readable configuration code is recognized as configuration information and the operation mode of the code scanner 110 is configured based on the analyzed machine-readable configuration code.

In addition, the code scanner 110 may transmit code information or digital images to the user interface system 104 depending on its current operation mode. The code scanner 110 is configured to automatically transmit either code information or a digital image to the user interface system 104 in response to a user input applied to the user input element 112. The code scanner 110 may also be configured to receive a control signal from the user interface system 104 that initializes an image capture operation performed by the code scanner 110. The code information and digital images may be further displayed on the display device 106.

The medical system 100 further includes a network 120 that is coupled to the user interface system 104 via connection 121, and a data server 122, that is coupled to the network 120 via connection 123. Network 120 may be any known communication network including a wireless network, a wired network, a public switched telephone network (PSTN), the Internet, and combinations thereof.

The code scanner 110 (i.e., the portable image capture device) may be coupled to the network 120 via connection 114, which may be a wired communication channel or a wireless communication channel. The code scanner 110 may communicate with the user interface system 104 or any other device connected to the network 120 via connection 114.

When communicating by way of network 120, the user interface system 104 may perform such functions as link layer and physical layer outroute coding and modulation (e.g., DVB-S2 adaptive coding and modulation), link layer and physical layer inroute handling (e.g., IPOS), inroute bandwidth allocation and load balancing, outroute prioritization, web acceleration and HTTP compression, flow control, encryption, redundancy switchovers, traffic restriction policy enforcement, data compression, TCP performance enhancements (e.g., TCP performance-enhancing proxies, such as TCP spoofing), quality of service functions (e.g., classification, prioritization, differentiation, random early detection (RED), TCP/UDP flow control), bandwidth usage policing, dynamic load balancing, and routing.

The data server 122 is a memory device configured to store an EMR for each patient. Each EMR includes respective patient data and is assigned to a unique patient ID that is also stored on the data server 122. The user interface system 104 is configured to access an EMR from the data server 122 via the network 120, and the display device 106 is configured to display data from a retrieved EMR. In addition, the data server 122 is configured to store and update patient information received from the user interface system 104 via the network 120. For example, the user interface system 104 may store patient data in a local memory or a cloud-based memory and transmit the patient data to the data server 122. The data server 122 may receive code information, information derived from code information, digital images, and/or metadata pertaining to the digital images from the user interface system 104 as the patient data. Here, the code information and digital images are acquired by the code scanner 110.

The medical system 100 may further include a medical device 130. The medical device 130 may be any type of patient monitoring, diagnostic, or therapeutic equipment, including, but not limited to, an ECG machine, an ultrasound machine, vital signs monitoring machine, and the like. The medical device 130 may be configured to read a biometric, physiological, diagnostic, and/or therapeutic attribute of a patient and generate medical data in digital or printable formats. The medical device 130 may further include a display device 131 configured to display patient information (e.g., an ECG reading, an ultrasound reading, a vital sign reading, etc.). In addition, the medical device 130 may be configured to print a reading onto a printable medium such as paper or film. In one example, the medical device 130 may be an ECG machine configured to print an ECG tracing 132 during patient monitoring. In another example, the medical device 130 may be operable to capture screenshots of images displayed on the display device 131, as is the case for ultrasound machines. Furthermore, the medical device 130 may be operable to acquire screenshots and output printed medical data.

Moreover, the medical device 130 may be optionally connected to the user interface system 104 via wired or wireless connection 133 and/or connected to the network 120 via wired or wireless connection 134. As such, the medical device 130 may be configured to communicate with the user interface system 104 via connection 133 or 134 or any other device connected to the network 120 via connection 134. In particular, the medical device 130 may be configured to transmit captured images (e.g., screenshots) to the user interface system 104 or to the data server 122. In addition, the medical device 130 may receive a control signal from the user interface system 104 to initialize an image capture, to initialize a transmission of captured images or both.

When set into image capture mode, the code scanner 110 may be used to capture a picture of either the display device 131 or the ECG tracing 132 in order to record an image of medical data corresponding to a patient. This feature may be particularly useful when the medical device 130 is not capable of outputting data, and particularly, digital images, to the user interface system 104 and/or the data server 122.

Figure 2:
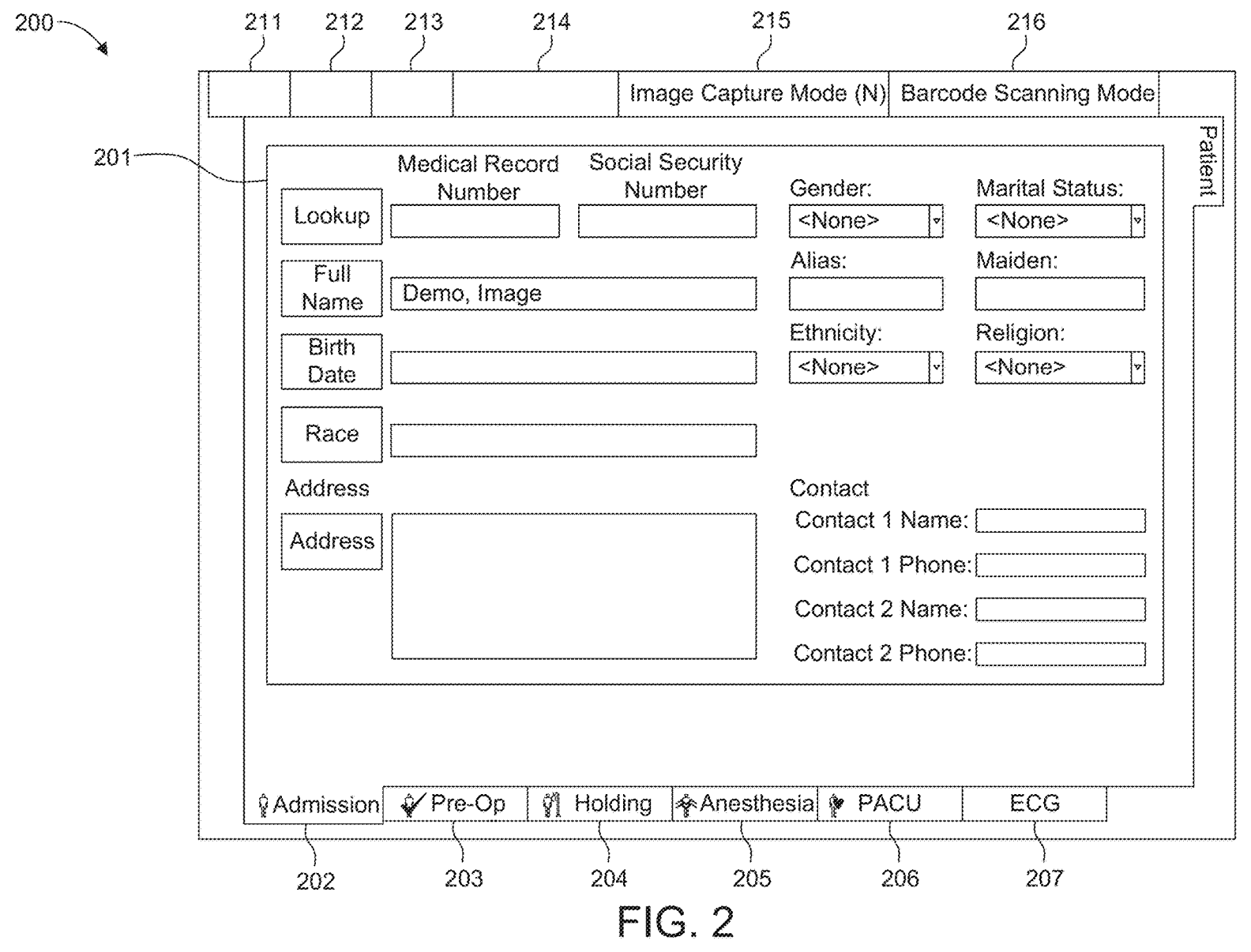

FIG. 2 illustrates a graphical user interface (GUI) 200 according to one or more embodiments. In particular, the GUI 200 is generated by the user interface system 104 in the course of running the EMR software, and is received by the display device 106 for display. GUI 200 displays a main menu for accessing, entering, and managing patient information. Thus, the GUI 200 may serve as a primary interface and access point to a patient's EMR. The GUI 200 is operable to receive user selections and inputs.

The GUI 200 may include a patient lookup and background information section 201, including various data fields of patient information entry and lookup.

The GUI 200 may include tabs 202-207 used to navigate to different stages of care provided to a patient. For example, admissions tab 202 may include patient data relevant to an admission stage of a patient, pre-op tab 203 may include patient data relevant to a pre-operation stage of the patient, holding tab 204 may include patient data relevant to a holding stage of the patient, anesthesia tab 205 may include patient data relevant to administering anesthesia to the patient, a Post Anesthesia Care Unit (PACU) tab 206 may include patient data relevant to a post-anesthesia stage or a post-operation stage of the patient, and an ECG tab 207 that enables a user to view captured images of ECG readings taken during the various stages of patient care in accordance with the one or more embodiments described herein. Additionally, or alternatively, captured ECG images may also be placed in an ECG section located within each tab 202-206. These images may be placed in a tab that corresponds to the stage of care during which the image was taken.

It will be appreciated that the foregoing tabs merely serve as an example, and should be treated as non-limiting such that some tabs may be removed and additional tabs may be included. For example, other captured images tabs and non-operating room tabs may be provided.

The GUI 200 may include icons 211-214 that provide user access to various types of patient chart data, including lab results, assigned staff, medication history, and use, vital signs, etc. In addition, the GUI 200 includes an image capture mode icon 215 and a code scanning mode icon 216. In response to a selection of the image capture mode icon 215 via user input, the user interface system 104 is configured to place the code scanner 110 into image capture mode if the code scanner 110 is currently in a different mode (e.g., code scanning mode) or maintain the code scanner 110 in the image capture mode if the code scanner 110 is currently in the image capture mode. The image capture mode icon 215 further includes an N symbol in parentheses. The N represents a number of images captured by the code scanner 110 that are currently saved and stored in the patient's EMR.

In addition, in response to a selection of the image capture mode icon 215 via user input, the user interface system 104 is configured to navigate the user to an image capture GUI 300 that will be further described in the context of FIGS. 3A and 3B. In particular, the image capture GUI 300 is launched by the user interface system 104 in response to a selection of the image capture mode icon 215. The launched GUI 300 is associated with a patient's EMR. Depending on its current operation mode, the user interface system 104 may reconfigure the code scanner 110 into image capture mode when the GUI 300 is launched. The GUI 300 is operable to receive user selections and inputs, and stores any saved data in the patient's EMR on the data server 122. Thus, the GUI 300 is linked to the patient's EMR via network 120. Images that are captured in the GUI 300 are automatically associated with a corresponding patient and are optionally stored in the patient's EMR based on further user input.

A selection of the code scanning mode icon 216 may set the code scanner 110 into code scanning mode, for example, for capturing ID information for identification purposes.

One of the operation modes of the code scanner 110 may be used by the user interface system 104 as a default mode. The default mode may be set by reading a machine-readable configuration code with the code scanner 110. The user interface system 104 is configured to determine the default mode by reading out a mode value. For example, while the GUI 300 is inactive (i.e., closed), the user interface system 104 may set or maintain the code scanner 110 into its default operation mode. For example, if the code scanning mode is configured as the default operation mode, the user interface system 104 will automatically set the code scanner 110 into code scanning mode while GUI 300 is closed. code scanner Here, the code scanning mode icon 216 could be optional since closing GUI 300 will result in the code scanner 110 being configured into code scanning mode.

The code scanner 110 is configured into image capture mode by the user interface system 104 when the GUI 300 is launched. Once a user has navigated to the image capture GUI 300 via image capture mode icon 215, the code scanner 110 is configured into image capture mode and the user may capture images using the code scanner 110 by manipulating the user input element 112. Upon triggering an image capture, the code scanner 110 is configured to capture an image and automatically upload the captured image to the user interface system 104 where it will be displayed in the image capture GUI 300 and thusly associated with a patient. The user interface system 104 also records a timestamp (e.g., a capture date and time) for each image capture, and stores the time stamp with the captured image. For example, the timestamp may be attached or applied directly to the captured image and stored therewith.

Captured images are automatically stored in a local memory or a cloud-based memory of the user interface system 104. However, these captured images may not be automatically stored on the data server 122 without further user action. Thus, a user may selectively determine which captured images viewable in GUI 300 should be saved to the data server 122, which captured images viewable in GUI 300 should be discarded from the local or cloud-based memory, and which saved images viewable in GUI 300 should be removed from the data server 122. As a result, a user may use the image capture GUI 300 not only to access captured images but also to manage the storage thereof within the patient's EMR.

The image capture GUI 300 may also include metadata fields that allow a user to enter and save metadata related to each captured image.

In response to a selection of the code scanning mode icon 216 via user input, the user interface system 104 is configured to place the code scanner 110 into code scanning mode if the code scanner 110 is currently in a different operation mode (e.g., image capture mode) or maintain the code scanner 110 in the code scanning mode if the code scanner 110 is currently in the code scanning mode.

By manipulating the image capture mode icon 215 and the code scanning mode icon 216, a user is able to quickly switch between operation modes of the code scanner 110 such that barcodes and digital images can be taken as needed without a cumbersome process.

Figure 3:
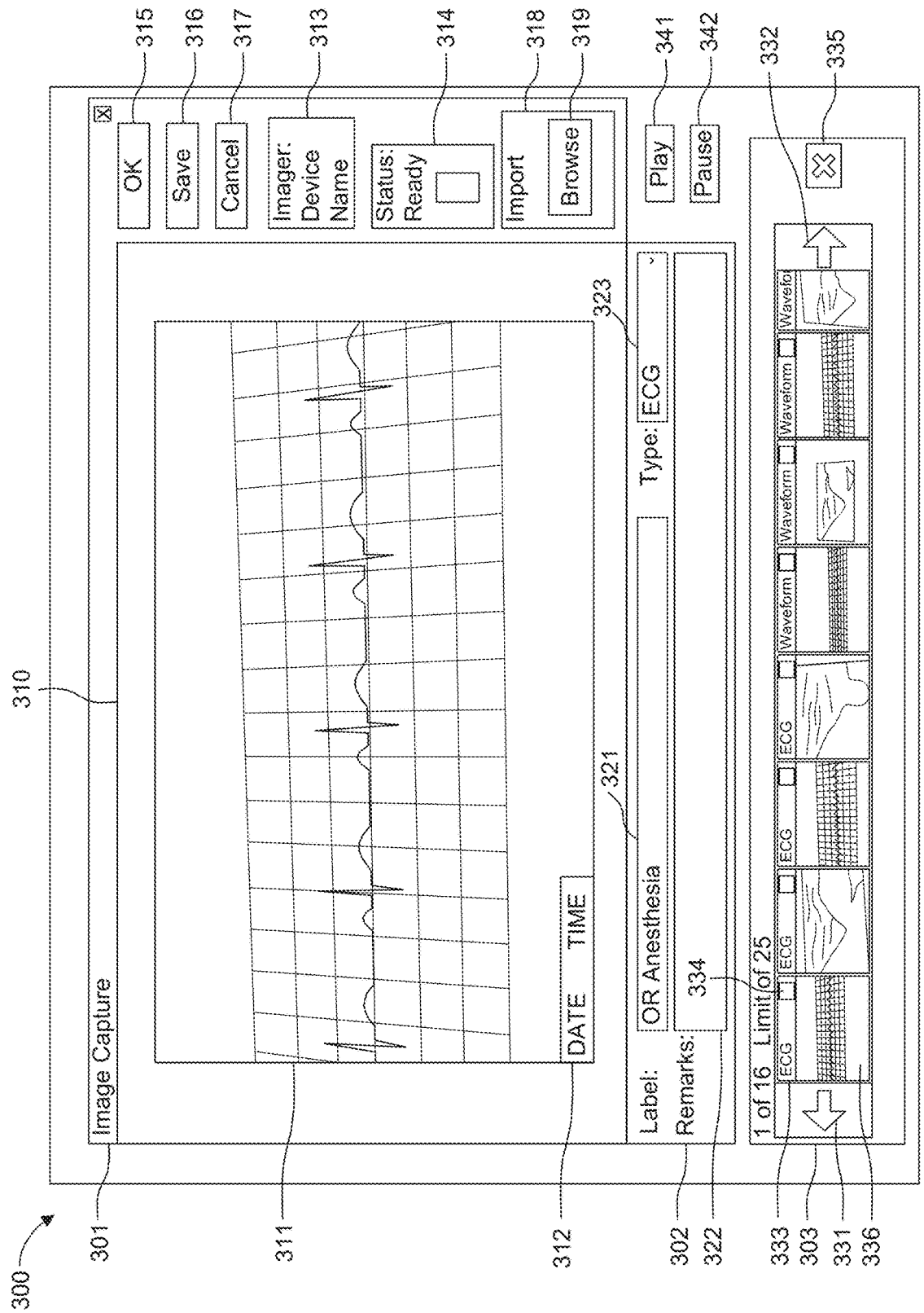
FIG. 3 illustrates a second GUI according to one or more embodiments.

FIG. 3 illustrates a GUI 300 according to one or more embodiments. In particular, FIG. 3 illustrates the GUI 300 subsequent to multiple image captures performed using the code scanner 110.

GUI 300 includes an image capture section 301, a metadata section 302, and a thumbnail section 303 that displays thumbnail images 330 of captured images.

When the GUI 300 is initially opened, the thumbnail section 303 displays thumbnails of any captured images there were obtained in a previous image capture session and saved in a patient's EMR in the data server 122.

Additionally, each thumbnail image 330 may be selectively activated by default or by user input. For example, when an image is initially captured using the code scanner 110, a thumbnail of that image is created by the user interface system 104 via the EMR software and automatically activated (i.e., selected or highlighted) for display in the image capture section 301. Other previously captured images may be viewed in the image capture section 301 by selecting its corresponding thumbnail.

The thumbnail section 303 further includes scroll icons 331 and 332 that enable a user to scroll through the thumbnail images 330 in two scrolling directions (e.g., right and left directions).

Each thumbnail image 330 includes a data type section 333 that displays a data type corresponding to the thumbnail image. Additionally, an activated thumbnail may be differentiated from other inactive thumbnails by changing a color or the data type section 333, for example.

Each thumbnail image 330 includes a selection box 334 that enables a user to select that particular thumbnail for deletion from the local memory and/or from the data server 122. To further enable this feature, the thumbnail section 303 includes a delete icon 335. Multiple thumbnail images 330 may be selected for deletion at a time. Here, multiple thumbnail images 330 are selected by activating respective selection boxes 334 and then deleted by subsequently clicking the delete icon 335. Captured images that correspond to selected and deleted thumbnails are removed from the local memory as well as from the data server 122, where applicable.

Each user may have different assigned permissions (e.g., read, write, and edit permissions) that authorize a user to delete captured images from the data server 122. If a user does not have edit permission, the user interface system 104, via the EMR software, will prevent the deletion of an image that is stored on the data server 122. A read permission permits a user to view previously captured images that are stored on the data server 122. A write permission permits a user to capture new images via the code scanner 110 and store them on the data server 122.

The image capture section 301 includes an image viewing area 310 in which a captured image 311 is displayed. In particular, the image viewing area 310 displays an image that is active amongst the thumbnail images 330. As noted above, when an image is initially captured using the code scanner 110, a thumbnail of that image is created by the user interface system 104 via the EMR software and automatically activated for display in the image capture section 301.

While a captured image is active, a user may enter metadata about the captured image in the metadata section 302. For example, the metadata section 302 may include a label field 321 corresponding to label or title related to the subject of the captured image, a remarks field 322 corresponding to additional comments a user may have regarding the captured image, and a data type field 323 corresponding to an image type or category related to the captured image. In the latter case, types of images may be selectable from the data type field 323 (e.g., via a drop-down listing) and may be related to the type of medical diagnostic information recorded in the image. For example, fields available in the data type field 323 may also correspond to tabs 202-207 such that a captured image is also placed in an appropriate tab that corresponds to the tab designated in the data type field 323. Here, the captured image 311 shown in this example is an image of an ECG tracing strip taken in anticipation of or during administration of anesthesia in an operating room. Thus, a user has chosen to label the image "OR Anesthesia" and selected "ECG" as the data type. The selected data type also appears in the data type section 333 of the corresponding thumbnail image 330.

In addition, a timestamp 312 is applied to the captured image 311 and stored therewith. Thus, the time stamp 312 is also displayed in the image capture section 301 along with the captured image 311.

The image capture section 301 includes a scanner ID field 313 that corresponds to the code scanner 110 currently connected to the user interface system 104 and a scanner status field 314 that indicates whether or not the code scanner 110 is ready to capture an image.

The image capture section 301 further includes additional icons, including an OK icon 315, a save icon 316, and a cancel icon 317.

Manipulating (i.e., selecting) the OK icon 315 results in any images and corresponding metadata captured during an image capture session (i.e., any images captured while GUI 300 is active after selecting the image capture mode icon 215) to be transferred from local memory of the user interface system 104 to the data server 122 via network 120 and stored in the patient's EMR at the data server 122.

Selecting the OK icon 315 further results in the EMR software exiting the GUI 300 and returning to the previous GUI (e.g., GUI 200). In other words, the EMR software exits the current image capture session.

Returning to the previous GUI further results in the user interface system 104 setting the code scanner 110 into an original or a previous operation mode the code scanner 110 was in at the time the user selected the image capture mode icon 215. For example, this could be the default operation mode of the code scanner 110. Thus, the code scanner 110 may be reverted back into code scanning mode in response to a selection of the OK icon 315. Alternatively, if the image capture mode is the default operation mode, the code scanner 110 may remain in the image capture mode as the software exits from GUI 300 and returns to the previous GUI. If the image capture mode is the default operation mode, the code scanner 110 may be placed into code scanning mode via user manipulation of the code scanning mode icon 216.

Manipulating the OK icon 315 may further result in any unsaved captured images, which were obtained during a current image capture session (i.e., not yet stored on the data server 122) and selectively removed using the delete icon 335, to not be saved in the patient's EMR on the data server 122 and removed from the local memory of the user interface system 104.

Manipulating the OK icon 315 may further result in any captured images, which have been previously saved to the data server 122 during the current image capture session (i.e., via the save icon 316) or during a previous image capture session and selectively removed using the delete icon 335, to be removed from the patient's EMR on the data server 122.

Manipulating the save icon 316 results in any images and corresponding metadata captured during an image capture session (i.e., any images captured while GUI 300 is active after selecting the image capture mode icon 215) to be transferred from local memory of the user interface system 104 to the data server 122 via network 120 and stored in the patient's EMR at the data server 122. However, in contrast to the OK icon 315, selecting the save icon 316 results in the EMR software remaining at the GUI 300 and further results in the code scanner 110 remaining in the image capture mode. In other words, the EMR software remains in the current image capture session.

Manipulating the save icon 316 may further result in any unsaved captured images, which were obtained during a current image capture session (i.e., not yet stored on the data server 122) and selectively removed using the delete icon 335, to not be saved in the patient's EMR on the data server 122 and removed from the local memory of the user interface system 104.

Manipulating the save icon 316 may further result in any captured images that have been previously saved to the data server 122 during the current image capture session (i.e., via the save icon 316) or during a previous image capture session and selectively removed using the delete icon 335 to be removed from the patient's EMR on the data server 122.

Manipulating the cancel icon 317 results in any images and corresponding metadata captured during an image capture session not being saved at the data server 122 and possibly or eventually removed from or overwritten in the local memory of the user interface system 104. As a result, unsaved images are not stored in the patient's EMR on the data server 122. In addition, the EMR software exits the current image capture session, returns to the previous GUI (e.g., GUI 200), and sets the code scanner 110 into an original or a previous operation mode (e.g., a default operation mode) in a similar manner described in reference to the OK icon 315.

Manipulating the cancel icon 317 may further result in canceling a removal or a deletion of any thumbnail images 330 that were removed using the delete icon 335 during the current image capture session.

The image capture GUI 300 may also include an import section 318 that includes a browse icon 319. The browse icon 319 is configured to enable a user to search for external storage devices that have medical images or medical videos stored thereon. An external storage device may be either the medical device 130 or a portable image capture device, such as the code scanner 110. By using the browse feature, a user may locate an external storage device, search for captured images (e.g., screenshots) and/or videos stored on the external storage device, and import selected images and/or videos into the GUI 300. By performing an import, the imported images and videos are stored in the local or cloud-based memory of the user interface system 104 and displayed within the image viewing area 310. The imported images and videos are also displayed in the thumbnail section 303 as a thumbnail image 330. By performing an import, the imported images and videos are automatically associated with a patient and a user may further determine whether to save the imported images and videos into the patient's EMR on the data server 122.

Figure 6:
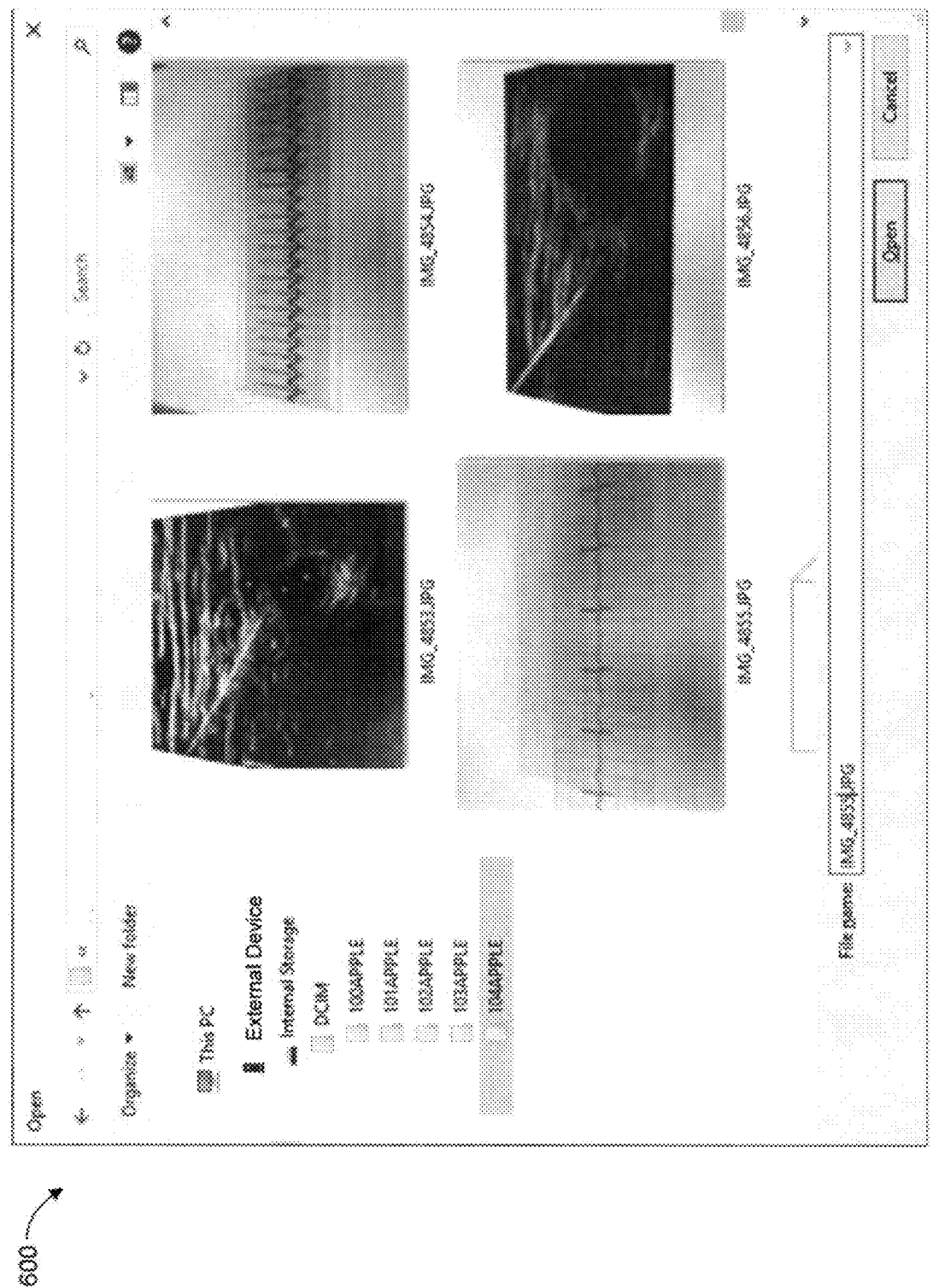
FIG. 6 illustrates a dialog box for importing files into the second GUI according to one or more embodiments.

Clicking the browse icon 319 may launch an additional dialog window (i.e., dialog window 600 shown in FIG. 6. The dialog window 600 enables a user to select from one or more storage devices, including any external storage device connected to the user interface system 104 through a direct connection or the network 120, and select image or video files stored on the selected storage device for importing to the user interface system 104 to be loaded into the GUI 300. Once imported, an image or a video is automatically associated with a patient that corresponds to the open GUI 300.

The image capture GUI 300 may also include a play icon 341 and a pause icon 342 that becomes enabled when a video is selected and displayed in the image viewing area 310, thereby enabling a user to control the playback of the video.

A Digital Imaging and Communications in Medicine (DICOM) file is comprised of one or more images and metadata that can be parsed. If a DICOM file (e.g., an ultrasound file) is selected through the browse function, the GUI 300 may be configured to show the images of the DICOM file as a slide show in the image viewing area 310. The associated metadata could be also be shown in the image viewing area 310.

Figure 4:
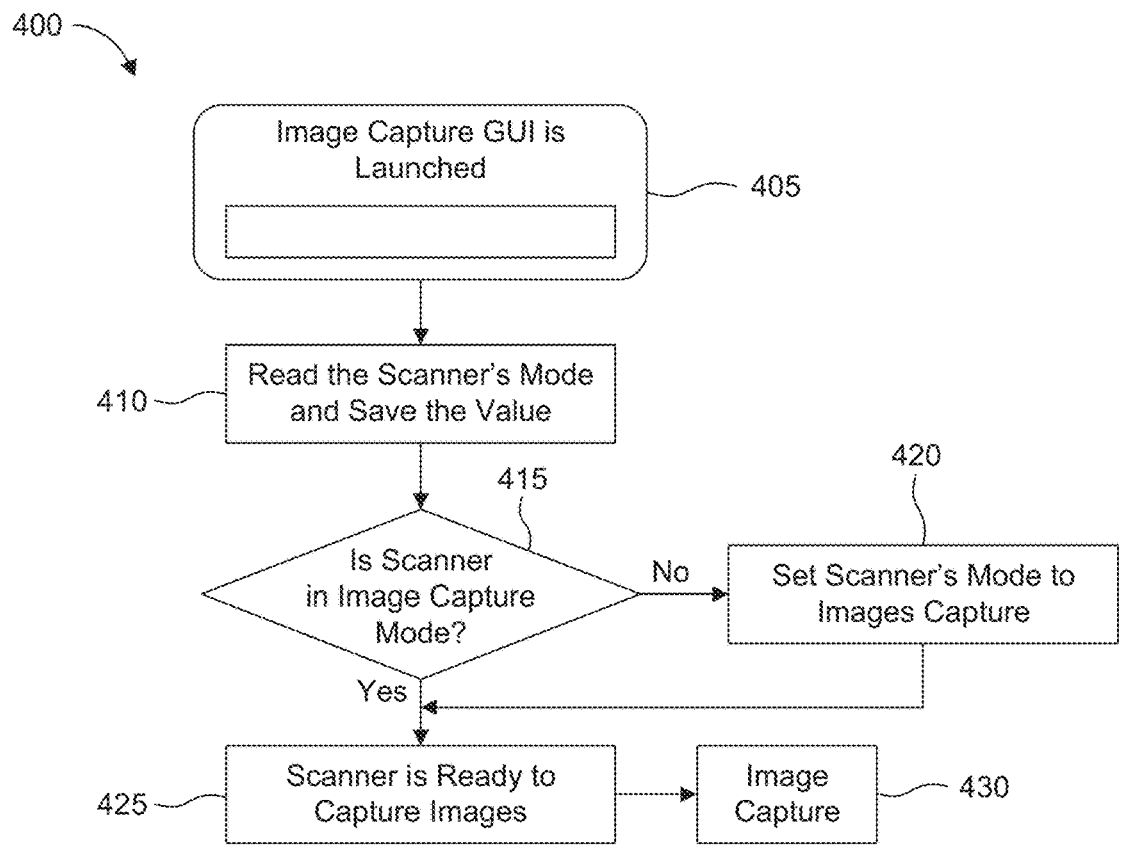
FIG. 4 is a flow diagram of an image capture operation according to one or more embodiments.

FIG. 4 is a flow diagram of an image capture operation 400 according to one or more embodiments.

In operation 405, a current image capture session is initialized by the manipulation of the image capture mode icon 215. As a result, image capture GUI 300 is launched by the user interface system 104 (via the EMR software) and displayed on the display device 106. At this time, the GUI 200 may either remain open (e.g., underneath the image capture GUI 300) so that it remains accessible to the user or it may be closed.

In operation 410, the user interface system 104 reads the original (i.e., current) operation mode of the code scanner 110 and saves a value corresponding to the original operation mode. The user interface system 104 may determine the original operation mode by obtaining operation mode status information from the code scanner 110. The user interface system 104 may obtain the operation mode status information by sending a request to the code scanner 110 or may continuously receive the operation mode status information from the code scanner 110. Each operation mode may be associated with a unique value. Thus, the user interface system 104 may store the value associated with the operation mode indicated in the operation mode status information in local memory. This saved value corresponds to the original operation mode the code scanner 110 was in just prior to a user selecting the image capture mode icon 215. This saved value is also used during the termination process 500.

In operation 415, the user interface system 104 determines whether the saved value of the original operation mode (i.e., the mode at the time the current image capture session is initialized) corresponds to the image capture mode. In other words, the user interface system 104 determines whether the code scanner 110 is already in the image capture mode at the time the current image capture session was initialized.

If no, the process flow proceeds to operation 420 where the user interface system 104 configures the code scanner 110 into image capture mode. Once configured into image capture mode, the process flow proceeds to operation 425, where the scanner status field 314 indicates that the code scanner 110 is ready to capture an image.

If yes, the process flow proceeds to operation 425 and the scanner status field 314 that indicates that the code scanner 110 is ready to capture an image.

In operation 430, a digital image 311 is captured by the user interface system 104 in response to a user input applied to the user input element 112 of the code scanner 110 and displayed in the image viewing area 310 along with its timestamp 312.

Figure 5:
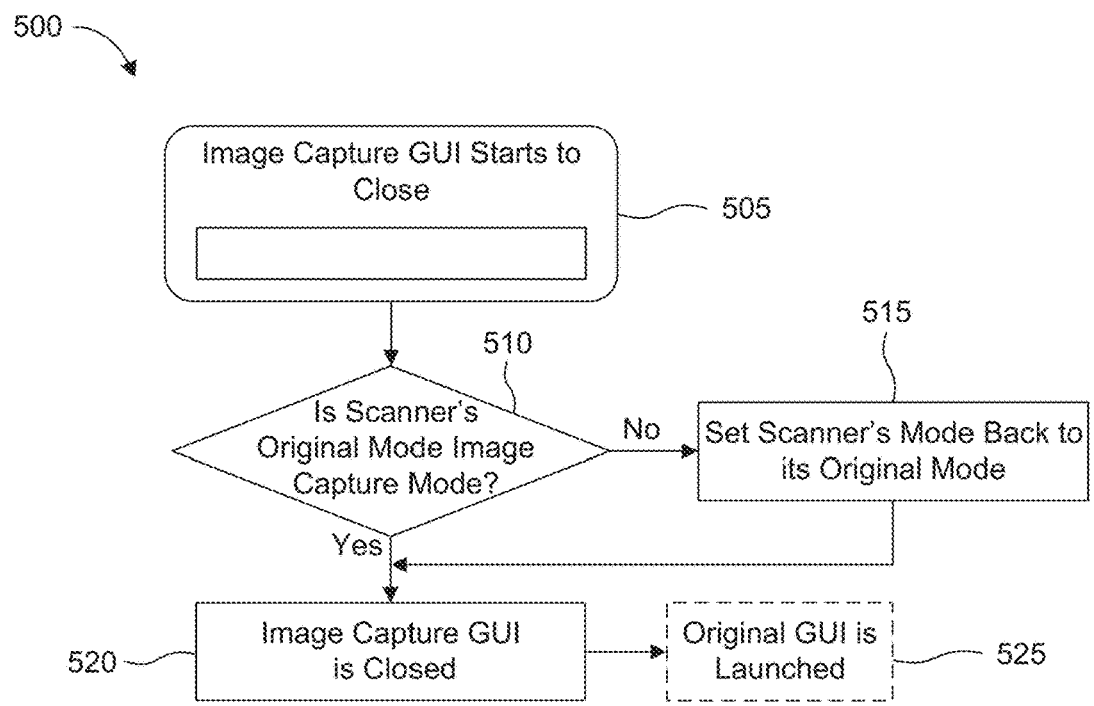
FIG. 5 is a flow diagram of a termination process of a current image capture session according to one or more embodiments.

FIG. 5 is a flow diagram of a termination process 500 of a current image capture session according to one or more embodiments.

In operation 505, the image capture GUI 300 begins to close and return to GUI 200 in response to a user manipulating either the OK icon 315 or the cancel icon 317, thereby initializing the termination process 500 of the current image capture session.

In operation 510, the user interface system 104 retrieves the saved value of the original operation mode obtained in operation 410 and determines whether the saved value corresponds to the image capture mode.

If no, the process flow proceeds to operation 515 where the user interface system 104 configures the code scanner 110 into the original capture mode associated with the saved value. For example, the code scanner 110 may be configured back into code scanning mode. After reconfiguring the operation mode of the code scanner 110, the process flow proceeds to operation 520.

If yes, the operation mode of the code scanner 110 is not altered and the process flow proceeds to operation 520.

In operation 520, the image capture GUI 300 is closed and the current image capture session is ended.

As a further option, if the GUI 200 was closed, minimized, or otherwise not viewable (e.g., in accordance with operation 405), the GUI 200 may be relaunched or made visible on the display device 106 in operation 525.

In view of the above, the user interface system 104 may use EMR software and the code scanner 110 to perform code reading as well as to capture a digital image of medically relevant information and store the digital image in the patient's EMR.

For example, the IMS 102 may be an anesthesia information management system (AIMS) and the EMR software may be anesthesia management software used to manage, track, and record the anesthesia care of a patient. The EMR may be an anesthesia record or may include an anesthesia record as part of the patient's complete EMR. As noted above, ECG measurements and tracings are of particular interest in an anesthesia record to document that condition of the patient before, during, and after the administering of anesthesia to a patient. The quality of the ECG strip would be adequate for anesthesia purposes as the intent is to illustrate the general heart rhythm condition of the patient prior to surgery. As a result, an anesthesia provider can easily store digital ECG measurements in the patient's EMR and access this information at a later time. As such, the IMS 102 provides a functional means to document the ECG. Image capture of readings from an electroencephalogram (EEG) may also be useful.

It may also be desirable to document other types of medical data with image capture. For example, health care providers may wish to take time-stamped photographs of a patient's teeth prior to and after a surgical procedure to document the state of a patient's teeth in the course of performing dental work or inserting an intubation tube. Namely, images could be useful to demonstrate that a patient's teeth were damages prior to the procedure and not due to the procedure itself.

In addition, the disclosed image capture may be used to capture medical data and images shown on a display of an ultrasound machine or in an ultrasound printout. Thus, the medical system 100 may be used to incorporate ultrasound images into a patient medical record.

In addition, the disclosed image capture may be used to document surgical markings (e.g., incision markings) on a patient's body prior to a surgical procedure.

In addition, the disclosed image capture may be used to incorporate images of blood product bags and other medications into a patient medical record to document that the correct product was given to a patient.

In addition, the disclosed image capture can be a medical device such as an implantable medical device that illustrates attributes such as part serial no., condition, location of insertion into the patient, and the like.

Integration of the code scanner 110 also allows the opportunity to provide additional functionality such as performing both code scanning and image capture using a single scanning device. Additionally, images of barcodes may be captured and stored for future reference.

By creating a location to receive and store captured images in the patient's EMR, the proposed system and methods enable network-wide access to the captured images. In addition, the proposed system and method can be used regardless of the equipment being used or equipment manufacturer. As a result, a standardized process for capturing medical data through the use of the proposed image capture system may be implemented. The use of such systems and methods can, for example, occur in any medical environment such as the scene of a medical event, an ambulance, a hospital, or a doctor's office.

While various embodiments have been disclosed, it will be apparent to those skilled in the art that various changes and modifications can be made which will achieve some of the advantages of the concepts disclosed herein without departing from the spirit and scope of the invention. It will be obvious to those reasonably skilled in the art that other components performing the same functions may be suitably substituted. It is to be understood that other embodiments may be utilized and structural or logical changes may be made without departing from the scope of the present invention. It should be mentioned that features explained with reference to a specific figure may be combined with features of other figures, even in those not explicitly mentioned. Such modifications to the general inventive concept are intended to be covered by the appended claims and their legal equivalents.

Furthermore, the following claims are hereby incorporated into the detailed description, where each claim may stand on its own as a separate example embodiment. While each claim may stand on its own as a separate example embodiment, it is to be noted that—although a dependent claim may refer in the claims to a specific combination with one or more other claims—other example embodiments may also include a combination of the dependent claim with the subject matter of each other dependent or independent claim. Such combinations are proposed herein unless it is stated that a specific combination is not intended. Furthermore, it is intended to include also features of a claim to any other independent claim even if this claim is not directly made dependent on the independent claim.

It is further to be noted that methods disclosed in the specification or in the claims may be implemented by a device having means for performing each of the respective acts of these methods. For example, the techniques described in this disclosure may be implemented, at least in part, in hardware, software, firmware, or any combination thereof, including any combination of a computing system, an integrated circuit, and a computer program on a non-transitory computer-readable recording medium. For example, various aspects of the described techniques may be implemented within one or more processors, including one or more microprocessors, DSPs, ASICs, or any other equivalent integrated or discrete logic circuitry, as well as any combinations of such components.

Further, it is to be understood that the disclosure of multiple acts or functions disclosed in the specification or in the claims may not be construed as to be within the specific order. Therefore, the disclosure of multiple acts or functions will not limit these to a particular order unless such acts or functions are not interchangeable for technical reasons. Furthermore, in some embodiments, a single act may include or may be broken into multiple sub acts. Such sub acts may be included and part of the disclosure of this single act unless explicitly excluded.

What is claimed is:

1. An electronic medical record (EMR) management system, comprising:
   a data server configured to store a plurality of EMRs for a plurality of patients, wherein each EMR is associated with a different one of the plurality of patients;
   an imaging device configured to capture an image medically related to a specific patient and transmit the captured image, wherein the imaging device is a scanner configured to read machine-readable codes in a code scanning mode and to capture images in an image capture mode;

an information management system arranged for managing medical data, the information management system communicatively coupled to the imaging device and to the data server, wherein the information management system is configured to receive the captured image from the imaging device, upon receiving the captured image, automatically associate the captured image with the specific patient, including associating the captured image with an EMR of the specific patient, and upon associating the captured image with the EMR of the specific patient, automatically store the captured image in the EMR of the specific patient in the data server; and, wherein the data server includes a database of patient identifiers (IDs), each being mapped to a different machine-readable code of a plurality of machine-readable codes, the scanner is configured to read a machine-readable code related to the specific patient and output code information representative of the machine-readable code to the information management system, and, the information management system is configured to analyze a format of the machine-readable code, determine whether the machine-readable code has a patient ID format, and, on a condition the machine-readable code has the patient ID format, receive from the data server a corresponding patient ID that is mapped to the machine-readable code.

2. The EMR management system of claim 1, wherein:
on a condition the machine-readable code does not have the patient ID format, the information management system is configured to record the machine-readable code as text corresponding to a medical item that is medically related to the specific patient.

3. The EMR management system of claim 1, wherein the information management system is an anesthesia information management system configured to manage, track, and record an anesthesia care of the specific patient.

4. The EMR management system of claim 1, wherein the information management system includes a user interface system configured to:
receive a first user input, and
configure the imaging device into the image capture mode based on the first user input.

5. The EMR system of claim 4, wherein the user interface system is configured to:
receive a second user input, and
configure the imaging device into the code scanning mode based on the second user input.

6. The EMR management system of claim 1, wherein:
the information management system includes a user interface system and a display device coupled to the user interface system,
wherein the user interface system is operable to launch a first graphical user interface (GUI) on the display device on a condition an image capture session is initialized by a first user input, and the user interface system is operable to configure the imaging device into the image capture mode for the image capture session in response to the first user input.

7. The EMR management system of claim 6, wherein:
the user interface system is operable to close the first GUI on the display device on a condition the image capture session is terminated by a second user input.

8. The EMR management system of claim 7, wherein the user interface system is operable to configure the imaging device in an original operation mode in response to the image capture session being terminated by the second user input, the original operation mode being an operation mode in which the imaging device was configured when the image capture session was initialized by the first user input.

9. The EMR management system of claim 8, wherein the original operation mode is the code scanning mode.

10. The EMR management system of claim 6, wherein the display device is configured to automatically display the captured images in the first GUI in response to the imaging device transmitting the captured images to the user interface system.

11. The EMR management system of claim 10, wherein:
the user interface system is operable to transmit the captured images to the data server in response to a second user input, and
wherein the data server is configured to automatically store the captured images in the EMR of the specific patient upon receipt.

12. The EMR management system of claim 6, wherein the user interface system is operable to display a second GUI on the display device, wherein the second GUI includes an image capture mode icon, which initializes the image capture session when selected by the first user input.

13. The EMR management system of claim 1, wherein the machine-readable codes includes at least one of barcodes, Quick Response (QR) codes, or radio-frequency identification (RFID) tags.

14. The EMR management system of claim 1, wherein the machine-readable code includes a pre-assigned prefix or suffix indicating that the machine-readable code relates to an identification of a patient.

15. The EMR management system of claim 1, wherein the information management system is configured to receive the machine-readable codes from the scanner and convert the codes into information identifying medical equipment, medication, or different types of medical fluid bags.

16. The EMR management system of claim 1, wherein the scanner is provided as a digital camera having a user input for acquiring an image.

17. The EMR management system of claim 1, wherein the information management system is configured to store the captured image in the EMR of the specific patient in response to a user input received after the captured image is associated with the specific patient.

18. The EMR management system of claim 1, wherein the information management system is configured to store the captured image in the EMR of the specific patient in response to the information management system associating the captured image with the specific patient.

* * * * *